United States Patent [19]
Bloch et al.

[11] 3,965,255
[45] June 22, 1976

[54] CONTROLLED DRUG RELEASING PREPARATIONS

[75] Inventors: René Bloch, Savion; Ora Kedem, Rehovoth; Ester Löbel, Hulon, all of Israel

[73] Assignee: E. E. Eljim Ecology Ltd., Rehovoth, Israel

[22] Filed: May 1, 1974

[21] Appl. No.: 466,018

[52] U.S. Cl............... 424/19; 424/20; 424/21; 424/22; 424/32; 424/33; 424/78
[51] Int. Cl.² ............... A61K 9/22; A61K 9/24; A61K 9/32; A61K 9/58
[58] Field of Search ............... 424/19–22, 424/32, 33, 78–83

[56] References Cited
UNITED STATES PATENTS

| | | | |
|---|---|---|---|
| 3,318,769 | 5/1967 | Folckemer et al. | 424/78 |
| 3,325,365 | 6/1967 | Hotko et al. | 424/33 |
| 3,710,795 | 1/1973 | Higuchi et al. | 128/260 |
| 3,737,521 | 6/1973 | Born | 424/22 |

FOREIGN PATENTS OR APPLICATIONS 2,135,022   1/1973   France

*Primary Examiner*—Shep K. Rose
*Attorney, Agent, or Firm*—Wallenstein, Spangenberg, Hattis & Strampel

[57] ABSTRACT

A drug delivery preparation with controlled release time and rate, comprising a therapeutic agent being encapsulated in or coated by a solvent membrane, as well as a process for the manufacture thereof, are disclosed.

9 Claims, No Drawings

CONTROLLED DRUG RELEASING PREPARATIONS

The present invention relates to a drug delivery preparation with controlled release time and rate and to a process for the preparation thereof.

It is very often desirable to supply a drug delivery preparation which releases the therapeutic agent at a constant rate in the course of a predetermined period of time. It is further desirable that said constant rate should be obtained very quickly, advantageously, instantaneously after the administration of the preparation. The same effect, namely relatively quick termination of the release should take place at the end of said predetermined period of time. This is in particular of importance in order to prevent overdosage and to minimize undesirable side effects.

The coventionally available tablets, pills, capsules and the like dissolve more or less instantaneously. The rate of release is not constant and the maximum absorption is gradually obtained after a certain period of time, whereafter it declines again gradually in the course of a relatively long period.

Sometimes, there are used capsules which are made of a material which has to be dissolved before the therapeutic agent is released. However, also with these capsules the above mentioned desired effect cannot be achieved as the moment the capsule is dissolved the situation is the same as for the above mentioned tablets, as also here the rate of release is not constant.

It has therefore been desirable to find some kind of preparation, which has such a mechanism of release by which the above drawbacks would be substantially overcome and in which the application of the therapeutic agent can be controlled in such a manner that a constant rate of release will be maintained for a predetermined period of time.

The present invention thus consists in a drug releasing preparation, adapted for oral administration which comprises a therapeutic agent being encapsulated in or coated by a solvent membrane as well as in a process of the manufacture thereof.

A solvent membrane or liquid membrane, in accordance with the present invention, comprises an immobilized, low molecular weight liquid or mixture of liquids, the molecular weight being less than about 1000. Examples of such membranes are described, for example, by Bloch et al., Nature, 199, 802–803, (1963) and by Vofsi et al., Naturwissenschaften, 61, 25–29 (1974).

More particularly, a solvent or liquid membrane, in accordance with the present invention, is a polymeric film made of a plasticiser or of a mixture of solvents serving as plasticisers and a certain amount of a polymer reinforcing said plasticiser. As the polymer there is preferably used a thermoplastic polymer. As examples of such polymers there can be named polyvinylchloride (PVC) and polyvinylacetate.

Suitable plasticisers may be chosen e.g. among adipates, sebacates, phosphates and phthalates. As examples of suitable plasticisers there can be named, e.g. Santicizer-B16 (butyl-phthalyl-butyl-glycolate from Monsanto); butyl-phthalyl-butyl-glycolate(Ciba-Geigy); Repoplast 39 (epoxidised soy bean oil from Ciba-Geigy); tri-tolyl-phosphate (BDH); dibutyl sebacate (Fluka); dioctyl sebacate (Grace); tri-(diethylhexyl)-phosphate (Silvia); 2-ethyl-hexyl-diphenyl phosphate; diisobutyl adipate (Grace); methyl stearate; glycerol glyceryl monooleate; Santicizer 160 (butyl-benzyl-phthalate from Monsanto); dibutyl sebacate (Ciba-Geigy); dioctyl-phthalate; diphenyl-octyl-phosphate (Disflamoll DOP from Bayer); diethyl phthalate (Palatinol A from BASF); di-(2-ethyl-hexyl)-phthalate (Palatinol AH from BASF) and TBP (BHD).

The release rate of such membranes is dependent on the amount of platiciser utilised. Thus by the variation of the amount of plasticiser the release rate can be varied. It is readily understood that the higher the amount of plasticiser the higher the release rate.

According to a preferred embodiment of the present invention, the plasticiser is present in the membrane in an amount of at least 40%, more preferably in an amount of at least 60% and particularly preferred in an amount of at least 80% by weight of the membrane. The upper limit of the amount of plasticiser in the solvent membrane is about 90% by weight.

A solvent or liquid membrane, in accordance with the present invention, means a membrane which is non-porous, i.e. the permeability of which is based on the dissolution of the permeating species, i.e. the therapeutic agent, in the membrane matrix and the subsequent diffusion thereof through said membrane. Moreover, said membrane should not be soluble in the digestive tract and be physiologically acceptable.

It is readily understood that by the preparation according to the present invention, the above purpose is substantially achieved, as it allows for the major period of the release:

a. A zero order release rate, i.e. a release of the therapeutic agent which depends on the vapor pressure of said agent in solid form, but is independent of the amount thereof. Said pressure has to be constant all the time during which the agent is being released from its solid form or from a saturated solution created by the osmotic influx of water.

b. Control of the release rate according to the specific requirements. The release and permeability rate is a function of the dissolution and the concentration gradient of the therapeutic agent in the membrane, the diffusion coefficient of said agent in the membrane, the thickness of the membrane, and of the vapor pressure of the therapeutic agent is solid form.

c. The control of the release time. Said release time is a function of the amount of the therapeutic agent present in the preparation and of the release rate. Therefrom the constant release of the therapeutic agent is ensured for a predetermined period of time.

From U.S. Pat. No. 3,710,795 and from German Specification DOS No. 2,054,488 there is known a drug delivery device for the continuous and controlled administration of a drug over a prolonged period of time. Said device comprises substantially:

a. a drug
b. a solid inner matrix in which said drug is dispersed; and
c. an outer polymeric membrane.

Said device has a serious drawback in that the release rate of the drug is governed by two different substances, namely the matrix and the membrane. This enables, if at all, only the use of drugs of which a small amount is to be released in the course of a relatively long period, i.e. implants.

The preparation according to the present invention comprises only one substance, which governs the release rate of the therapeutic agent, i.e. it is dependent on less variable parameters. Moreover, it can be utilised for both slow- and quick releasable therapeutic agents.

The precise control of the release rate may be achieved by:

a. The proper selection of the membrane.

b. That constant vapor pressure of the therapeutic agent. In case that said pressure is too high, said agent may be admixed with a pharmaceutically acceptable additive, provided that a homogeneous mass is obtained which has a constant vapor pressure.

c. The variation of the capsule area, sometimes by changing the release surface by way of micro encapsulation.

As therapeutic agent practically any drug can be utilised, provided it has a vapor pressure which is high enough to ensure the desired release rate for a given membrane. Thus, for example, there should be mentioned inter alia, antibiotics, e.g. tetracycline; tranquilizers e.g. benzodiazepines, e.g. diazepam or chlorazepoxide; steriods e.g. estrogens; vitamins, e.g. vitamin B and C; anti-histamines, e.g. chropheniramine; stimulants, e.g. amphetamide; arrhythmic agents, e.g. procainamide; and other therapeutic agents, e.g. digitalis, antipyrine and the like.

It is readily understood that for each therapeutic agent and/or for each specific required level of drug in the human body the specific membrane has to be chosen.

Very often it is advantageous to add some additional substance, e.g. a filler, such as lactose, starch, calcium phosphate or the like. Such a filler ascertains that a pill of a practical size is being obtained. Moreover, it ascertains a good contact with the membrane. It is readily understood that neither the filler nor any other additional substance added should have any influence on the release rate of the therapeutic agent.

The drug releasing preparations of the present invention can be prepared by encapsulating or coating the pure drug or, if desired, a mixture of the drug and one or more inert ingredients, in or with a film of a solvent membrane, according to methods known per se. Thus, for example, a pill or a tablet of the therapeutic agent can be prepared in that said agent is dipped, if desired, together with an additional substance, e.g. a filler, into a solution comprising a suitable solvent, at least one plasticiser or mixture of solvents serving as plasticisers and at least on polymer, whereafter the solvent is evaporated.

According to another method, a pill or a tablet of the therapeutic agent, if desired, together with an additional substance, e.g. a filler, is covered with a solvent membrane, which is then closed by a dielectric sealing procedure well known in the art.

The present invention will now be illustrated with reference to the following examples, without being limited by them.

EXAMPLE 1

A table was prepared by direct compression of 3 mg digitalis and 300 mg lactose. The table was immersed shortly in a solution containing 90% by weight cyclohexanone, 8% by weight dioctylphthalate (DOP) and 2% by weight polyvinylchloride (P.V.C.). The solvent cyclohexanone was removed in an oven at 40°C during a period of 6 hours.

The coated table was suspended into 100 ml water and the release of digitalis from the preparation was measured as function of time. Amounts released were:

| | |
|---|---|
| First hour | 0.68 mg |
| Second hour | 0.74 mg |
| Third hour | 0.70 mg |
| Fourth hour | 0.78 mg |
| Fifth hour | 0.08 mg |
| Sixth hour | undetectable |

EXAMPLE 2

A tablet was prepared as in Example 1 containing 10 mg antipyrine dispersed in 200 mg lactose. The ratio of P.V.C. to DOP was 1:9. Release rates determined as in example 1 were:

| | |
|---|---|
| First hour | 1.28 mg |
| Second hour | 1.42 mg |
| Third hour | 1.36 mg |
| Fourth hour | 1.54 mg |
| Fifth hour | 1.48 mg |
| Sixth hour | 1.38 mg |
| Seventh hour | 1.42 mg |
| Eighth hour | 0.06 mg |

EXAMPLE 3

A tablet was prepared by compressing 10.5 mg of procainamide hydrochloride on top of 100 mg of lactose. The tablet obtained has a diameter of 1.3 cm. It was covered on both sides with a membrane having a thickness of about 100 $\mu$.

The membrane was prepared from:

| | |
|---|---|
| PVC | 16.6% (by weight) |
| 2-Ethyl-hexyl-diphenyl phosphate | 66.8% (by weight) |
| N,N-Dimethyl lauramide | 16.6% (by weight) |

The membrane was prepared as follow:

The membrane components were dissolved and mixed together in cyclohexanone. The solution obtained was spread on a glass plate with a knife and left to evaporate to dryness. The dry membrane obtained was pealed off the glass plate and used to cover the tablet. The membrane was sealed around the tablet by a dielectric sealing method, which is known per se.

A coated tablet prepared as described above was immersed in 100 ml water and the water was slowly agitated. The release of procainamide hydrochloride through the membrane into the water was as folows:

| | |
|---|---|
| First hour | 1.8 mg |
| Second hour | 1.8 mg |
| Third hour | 2.6 mg |
| Fourth hour | 2.6 mg |
| Fifth hour | 1.4 mg |
| Sixth hour | 0.3 mg |
| Seventh hour | No release. |

Example 4

A tablet having a diameter of 1.3 cm and comprising 10 mg of atropin sulfate and 100 mg of lactose was prepared as described in Example 3. The tablet obtained was encapsulated in a membrane as described in example 3. The membrane utilised had the following composition:

| | |
|---|---|
| PVC | 20% (by weight) |
| 2-Ethyl-hexyl-diphenyl phosphate | 60% (by weight) |

| | |
|---|---|
| -continued | |
| N,N-Dimethyl lauramide | 20% (by weight) |

The membrane was prepared as described in Example 3.

A coated tablet was immersed in 20 ml of water which was slowly agitated. The release of the atropin sulfate into the water was nearly constant for 7 hours 0.3 mg/hour.

EXAMPLE 5 a. A preparation was produced in a similar manner as described in Example 3.

The tablet had the following composition:

| | |
|---|---|
| Theophylline | 5 mg |
| Starch | 100 mg |

The membrance had the following composition:

| | |
|---|---|
| PVC | 20% (by weight) |
| 2-Ethyl-hexyl-diphenyl phosphate | 80% (by weight) |

The release of the theophylline was measured for 45 hours. The release rate was nearly constant 0.12 mg/hour.

b. 0.45 mg of theophylline was put on an aluminium foil which served as an inert support in putting it thereon in water and thereafter evaporating the water. Thereafter it was coated in the same manner with the same membrane as in (a). The diameter of the preparation was 0.6 cm.

The release of the theopylline into water was measured for 7 hours. The release rate was nearly constant 0.045 mg/hour.

EXAMPLE 6

A preparation was produced in a similar manner as described in Example 3.

The tablet had the following composition:

| | |
|---|---|
| Dicumarol | 5 mg |
| Lactose | 100 mg |

The membrane had the following composition:

| | |
|---|---|
| PVC | 12.5% (by weight) |
| Diphenylactyl phosphate | 75% (by weight) |
| N,N-Dimethyl lauramide | 12.5% (by weight) |

The release of dicumarol into water was measured for 3 hours and samples were taken each one-half hour. The release rate was constant 0.12 mg/hour.

EXAMPLE 7

A preparation was produced in a similar manner as described in Example 3.

The tablet had the following composition:

| | |
|---|---|
| Antipyrine | 13 mg |
| Lactose | 100 mg |

The membrane had the following composition:

| | |
|---|---|
| PVC | 20% (by weight) |

| | |
|---|---|
| -continued | |
| Butyl phthalyl butyl glycolate | 80% (by weight) |

The following release rates were determined:

| | |
|---|---|
| First hour | 1 mg/hour |
| 7 following hours | 1.3 mg/hour |
| 2 following hours | 0.3 mg/hour |
| 2 following hours | 0.2 mg/hour |
| 2 following hours | 0.15 mg/hour |
| 4 following hours | 0.12 mg/hour |
| 6 following hours | 0.08 mg/hour |

Thereafter no further release could be observed.

EXAMPLE 8

A preparation was produced in a similar manner as described in Example 3.

The tablet had the following composition:

| | |
|---|---|
| Diazepam | 5 mg |
| Starch | 100 mg |

The membrane had the following composition:

| | |
|---|---|
| PVC | 20% (by weight) |
| Diphenyl-octyl phosphate | 80% (by weight) |

The preparation obtained was slowly agitated in a 0.1 molar HCL solution. The following release rates were determined:

| | |
|---|---|
| First hour | 0.8 mg |
| Second hour | 0.8 mg |
| Third hour | 0.8 mg |
| Fourth hour | 0.8 mg |
| Fifth hour | 0.2 mg |
| Sixth hour | 0.12 mg |

During the following 17 hours altogether 0.2 mg of diazepam were released.

EXAMPLE 9

In this and in the following Example 10 the release rate of therapeutic agent through a given membrane is shown in a diffusion cell. This cell consists of two half cells of perspex between which the membrane is clamped, which membrane corresponds to the membrane in the previous Examples. One half cell contains the drug in its pure form (i.e. as a liquid) or as a saturated solution. The second half cell contains a 0.01 molar HCl solution.

About 10 mg of amitriptyline as liquid were placed into the first half cell (feeding compartment). Said feeding compartment was separated from the second half cell (accepting compartment) by a membrane having the following composition:

| | |
|---|---|
| PVC | 25% (by weight) |
| Santicizer 334F (Monsanto) | 75% (by weight) |

The membrane thickness was about 150 $\mu$ and its area 2 $cm^2$. The accepting compartment was stirred with a magnetic stirrer and samples were withdrawn for analysis. The average rate of release in the course of 20 hours was about 0.22 $mg/cm^2/hour$.

EXAMPLE 10

In a similar manner as described in Example 9, the release rate of dehydroemetin was determined in a diffusion cell. The separating membrane had the following composition:

| | |
|---|---|
| PVC | 25% (by weight) |
| Diisobutyladipate | 75% (by weight) |

The thickness of the membrane was about 120 $\mu$ and its area 2 cm$^2$.

Both compartments were stirred with magnetic stirrers and the temperature was room temperature.

The release rate for the first 4 hours was about 0.9 mg/cm$^2$/hour and for the following hours about 0.42 mg/cm$^2$/hour.

Having now particularly described and ascertained the nature of our said invention and in what manner the same is to be performed, we declare that what we claim is:

1. A zero order release rate drug releasing preparation adapted for oral administration and for the controlled release of the drug contained therein at a substantially constant release rate during the first hour after administration and for several hours thereafter, which preparation comprises a drug body encapsulated in or coated with an outer solvent member, said drug body being selected from the group consisting of pure drug and drug admixed with an additional substance or substances which do not substantially influence the zero order release rate of the drug in said drug releasing preparation, and said solvent membrane comprising at least one plasticizer and at least one reinforcing polymer, which membrane is essentially insoluble in the digestive tract, the plasticizer content constituting from about 40 to about 90% by weight of the solvent membrane, said solvent membrane in the as prepared drug releasing preparation being substantially free of drug.

2. A drug releasing preparation according to claim 1, wherein plasicizer is 2-Ethyl-hexyl-diphenyl phosphate and the polymer reinforcing said plasticizer is polyvinyl chloride.

3. A drug releasing preparation according to claim 1, wherein the reinforcing polymer is a thermoplastic polymer.

4. A drug releasing preparation according to claim 3, wherein the polymer is selected from the group consisting of polyvinylchloride and polyvinylacetate.

5. A drug releasing preparation according to claim 1, wherein the plasticiser is selected from the group consisting of adipates, sebacates, phosphates and phthalates.

6. A drug releasing preparation according to claim 4 wherein the plasticiser is selected from the group consisting of butyl-phthalyl-butyl-glycolate, epoxidised soy bean oil, tritolyl-phosphate, dibutyl sebacate, dioctyl sebacate, tri-(diethyl-hexyl)-phosphate, 2-ethyl-hexyl-diphenyl phosphate, di-iso-butyl-adipate, methyl stearate, glycerol glyceryl monooleate, butyl-benzyl phthalate, dioctyl phthalate, diphenyl-octyl phosphate, di-ethyl phthalate, di-(2-ethyl-hexyl)-phthalate and TBP.

7. A drug releasing preparation according to claim 1, wherein the plasticiser content is at least about 80% by weight of the weight of the solvent membrane.

8. A drug releasing preparation according to claim 1, wherein the therapeutic agent is selected from the group consisting of steroids, vitamins, antihistamines, stimulants, tranquilizers. antibiotics and arrhytmic agents.

9. A drug releasing preparation according to claim 8, wherein the therapeutic agent is selected from the group consisting of digitalis, antipyrine, procainamide hydrochloride, atropine sulfate, theophylline and dicumarol, diazepam, amitriptyline and dehydroemetine.

* * * * *